United States Patent
Wu

(10) Patent No.: US 11,345,926 B2
(45) Date of Patent: May 31, 2022

(54) TRANSPOSON SYSTEM, KIT COMPRISING THE SAME, AND USES THEREOF

(71) Applicant: GenomeFrontier Therapeutics, INC., Grand Cayman (KY)

(72) Inventor: Sareina Chiung-Yuan Wu, Taipei (TW)

(*) Notice: Subject to any disclaimer, the term of this patent is extended or adjusted under 35 U.S.C. 154(b) by 290 days.

(21) Appl. No.: 15/766,707

(22) PCT Filed: Dec. 12, 2016

(86) PCT No.: PCT/CN2016/109510
§ 371 (c)(1),
(2) Date: Apr. 6, 2018

(87) PCT Pub. No.: WO2017/101749
PCT Pub. Date: Jun. 22, 2017

(65) Prior Publication Data
US 2018/0320196 A1    Nov. 8, 2018

Related U.S. Application Data

(60) Provisional application No. 62/267,270, filed on Dec. 14, 2015.

(51) Int. Cl.
| *C12N 15/85* | (2006.01) |
| *C12N 9/22* | (2006.01) |
| *C12N 15/90* | (2006.01) |

(52) U.S. Cl.
CPC ............... *C12N 15/85* (2013.01); *C12N 9/22* (2013.01); *C12N 15/8509* (2013.01); *C12N 15/90* (2013.01); *C12N 15/907* (2013.01); *C12N 2510/00* (2013.01); *C12N 2800/90* (2013.01)

(58) Field of Classification Search
CPC ...... C12N 15/85; C12N 15/90; C12N 15/907; C12N 2510/00; C12N 2800/90; C12N 9/22; A61P 29/00; A61P 31/00; A61P 35/00; A61P 35/02; A61P 37/02; A61P 37/08; A61P 43/00
USPC ................................................. 435/455, 463
See application file for complete search history.

(56) References Cited

U.S. PATENT DOCUMENTS

| 2002/0173634 | A1 | 11/2002 | Fraser et al. | |
| 2009/0042297 | A1 | 2/2009 | George et al. | |
| 2015/0283267 | A1* | 10/2015 | Vandendriessche ... | C12N 15/86 514/44 R |

FOREIGN PATENT DOCUMENTS

| CN | 101297031 A | 10/2008 |
| CN | 102421902 A | 4/2012 |
| CN | 102943092 A | 2/2013 |
| DE | 10/2011/118018 A1 | 4/2013 |
| WO | WO-2015/139093 A1 | 9/2015 |
| WO | WO-2015/157579 A2 | 10/2015 |

OTHER PUBLICATIONS

Meir et al. (2013, FASEB Journal, vol. 27, pp. 4429-4443). (Year: 2013).*
Chen et al. Human Gene Therapy 16:126-131 (Jan. 2005) (Year: 2005).*
Nakazawa et al. J Immunother. Oct. 2009 ; 32(8): 826-836. (Year: 2009).*
Nakazawa et al "Optimization of the *PiggyBac* Transposon System for the Sustained Genetic Modification of Human T-Lymphocytes" Journal of Immunotherapy vol. 32, pp. 826-836, 2009.
Feschotte "The *piggyback* Transposon Holds Promise for Human Gene Therapy" PNAS vol. 103, pp. 14981-14982, 2006.
Meir et al "A Versatile, Highly Efficient, and Potentially Safer *piggyback* Transposon System for Mammalian Genome Manipulations" The FASEB Journal vol. 27, pp. 4429-4443, 2013.
Meir et al "Genome-Wide Target Profiling of *piggyback* and Tol2 in HEK 293: Pros and Cons for Gene Discovery and Gene Therapy" BMC Biotechnology vol. 11, pp. 1-19, 2011.
Meir et al "Transposon-Based Vector Systems for Gene Therapy Clinical Trials: Challenges and Considerations" Chang Gung Medical Journal vol. 34, pp. 565-579, 2011.
Troyanovsky et al "The Functionality of Minimal *piggyback* Transposons in Mammalian Cells" Molecular Therapy Nucleic Acids vol. 5, abstract, 2016.
Wu et al "*piggyback* is a Flexible and Highly Active Transposon as Compared to *Sleeping Beauty*, Tol2, and Mos1 in Mammalian Cells" PNAS vol. 103, pp. 15008-15013, 2006.
Xie et al "Current Advance of *piggyback* in Mammals and Mammalian Cells" Chinest Bulletin of Life Sciences vol. 23, pp. 255-260, 2011.

* cited by examiner

*Primary Examiner* — Janet L Epps-Smith

(57) ABSTRACT

An in vitro method for integrating an exogenous DNA sequence into the genome of a cell using a transposon system. The transposon system includes a first vector carrying inverted repeat sequences and an exogenous DNA, and a second vector that expresses a transposases. Also provided is a kit including the transposon system for integrating an exogenous DNA into the genome of a cell. A method for treating a subject is described that includes engineering an immune cell to carry an exogenous DNA sequence using the method and/or the kit described above and administering an effective amount of the engineered immune cell to the subject.

12 Claims, 4 Drawing Sheets

Specification includes a Sequence Listing.

SEQUENCE LISTING

<160> NUMBER OF SEQ ID NOS: 8

<210> SEQ ID NO 1
<211> LENGTH: 67
<212> TYPE: DNA
<213> ORGANISM: Artificial Sequence
<220> FEATURE:
<223> OTHER INFORMATION: synthetic sequence-5-IR

<400> SEQUENCE: 1
ttaaccctag aaagataatc atattgtgac gtacgttaaa gataatcatg cgtaaaattg    60
acgcatg                                                              67

<210> SEQ ID NO 2
<211> LENGTH: 40
<212> TYPE: DNA
<213> ORGANISM: Artificial Sequence
<220> FEATURE:
<223> OTHER INFORMATION: synthetic sequence-3-IR

<400> SEQUENCE: 2
gcatgcgtca attttacgca gactatcttt ctagggttaa                          40

<210> SEQ ID NO 3
<211> LENGTH: 2697
<212> TYPE: DNA
<213> ORGANISM: Artificial Sequence
<220> FEATURE:
<223> OTHER INFORMATION: synthetic sequence-ThyPLGMH

<400> SEQUENCE: 3
atgggtcgca agaaacgtcg ccaacgtcgc cgtccgccta tcatgactcg agccatgggc    60
agcagcctgg acgacgagca catcctgagc gccctgctgc agagcgacga cgagctggtc   120
ggcgaggaca gcgacagcga ggtgagcgac cacgtgagcg aggacgacgt gcagtccgac   180
accgaggagg ccttcatcga cgaggtgcac gaggtgcagc ctaccagcag cggctccgag   240
atcctggacg agcagaacgt gatcgagcag cccggcagct ccctggccag caacaggatc   300
ctgacccctg cccagaggac catcaggggc aagaacaagc actgctggtc cacctccaag   360
cccaccaggc ggagcagggt gtccgccctg aacatcgtga agccagag gggcccacc     420 aggatgtgca ggaacatcta cgacccctg ctgtgcttca gctgttctt caccgacgag   480 atcatcagcg agatcgtgaa gtggaccaac gccgagatca gcctgaagag gcgggagagc   540
atgacctccg ccaccttcag ggacaccaac gaggacgaga tctacgcctt cttcggcatc   600
ctggtgatga ccgccgtgag gaaggacaac cacatgagca ccgacgacct gttcgacaga   660
tccctgagca tggtgtacgt gagcgtgatg agcagggaca gattcgactt cctgatcaga   720

-continued

```
tgcctgagga tggacgacaa gagcatcagg cccaccctgc gggagaacga cgtgttcacc      780
cccgtgagaa agatctggga cctgttcatc caccagtgca tccagaacta cacccctggc      840
gcccacctga ccatcgacga gcagctgctg ggcttcaggg gcaggtgccc cttcagggtc      900
tatatcccca caagcccag caagtacggc atcaagatcc tgatgatgtg cgacagcggc       960
accaagtaca tgatcaacgg catgccctac ctgggcaggg caccagac caacggcgtg       1020 cccctgggcg agtactacgt gaaggagctg tccaagcccg tccacggcag ctgcagaaac     1080
atcacctgcg caactggtt caccagcatc ccctggcca agaacctgct gcaggagccc       1140
tacaagctga ccatcgtggg caccgtgaga agcaacaaga gagagatccc cgaggtcctg     1200
aagaacagca ggtccaggcc cgtgggcacc agcatgttct gcttcgacgg ccccctgacc     1260
ctggtgtcct acaagcccaa gcccgccaag atggtgtacc tgctgtccag ctgcgacgag    1320
gacgccagca tcaacgagag caccggcaag ccccagatgg tgatgtacta caaccagacc     1380
aagggcggcg tggacaccct ggaccagatg tgcagcgtga tgacctgcag cagaaagacc     1440
aacaggtggc ccatggccct gctgtacggc atgatcaaca tcgcctgcat caacagcttc     1500
atcatctaca gccacaacgt gagcagcaag ggcgagaagg tgcagagccg aaaaagttc     1560 atgcggaacc tgtacatggg cctgacctcc agcttcatga ggaagaggct ggaggcccc    1620 accctgaaga gatacctgag gacaacatc agcaacatcc tgcccaaaga ggtgcccggc     1680
accagcgacg acagcaccga ggagcccgtg atgaagaaga ggacctactg cacctactgt    1740
cccagcaaga tcagaagaaa ggccagcgcc agctgcaaga agtgtaagaa ggtcatctgc    1800
cgggagcaca acatcgacat gtgccagagc tgtttcaagc ttaagttggg cggcggcgcc    1860
cccgccgtgg gcggcggccc caaggccgcg gataaaccgg tcgccaccat ggtgagcaag    1920
ggcgaggagc tgttcaccgg ggtggtgccc atcctggtcg agctggacgg cgacgtaaac    1980
ggccacaagt tcagcgtgtc cggcgagggc gagggcgatg ccacctacgg caagctgacc    2040
ctgaagttca tctgcaccac cggcaagctg cccgtgccct ggcccaccct cgtgaccacc    2100
ctgacctacg gcgtgcagtg cttcagccgc taccccgacc acatgaagca gcacgacttc    2160
ttcaagtccg ccatgcccga aggctacgtc caggagcgca ccatcttctt caaggacgac    2220
ggcaactaca agacccgcgc cgaggtgaag ttcgagggcg acaccctggt gaaccgcatc    2280
gagctgaagg gcatcgactt caaggaggac ggcaacatcc tggggcacaa gctggagtac    2340
aactacaaca gccacaacgt ctatatcatg gccgacaagc agaagaacgg catcaaggtg    2400
aacttcaaga tccgccacaa catcgaggac ggcagcgtgc agctcgccga ccactaccag    2460
cagaacaccc ccatcggcga cggccccgtg ctgctgcccg acaaccacta cctgagcacc    2520
cagtccgccc tgagcaaaga ccccaacgag aagcgcgatc acatggtcct gctggagttc    2580
gtgaccgccg ccgggatcac tctcggcatg gacgagctgt acaagcttgg gcccgaacaa    2640
aaactcatct cagaagagga tctgaatagc gccgtcgacc atcatcatca tcatcat       2697
```

<210> SEQ ID NO 4
<211> LENGTH: 899
<212> TYPE: PRT
<213> ORGANISM: Artificial Sequence
<220> FEATURE:
<223> OTHER INFORMATION: synthetic sequence-ThyPLGMH

<400> SEQUENCE: 4

Met Gly Arg Lys Lys Arg Arg Gln Arg Arg Pro Pro Ile Met Thr
1               5                   10                  15

-continued

Arg Ala Met Gly Ser Ser Leu Asp Asp Glu His Ile Leu Ser Ala Leu
            20                  25                  30

Leu Gln Ser Asp Asp Glu Leu Val Gly Glu Asp Ser Asp Ser Glu Val
        35                  40                  45

Ser Asp His Val Ser Glu Asp Val Gln Ser Asp Thr Glu Glu Ala
50                  55                  60

Phe Ile Asp Glu Val His Glu Val Gln Pro Thr Ser Ser Gly Ser Glu
65                  70                  75                  80

Ile Leu Asp Glu Gln Asn Val Ile Glu Gln Pro Gly Ser Ser Leu Ala
                85                  90                  95

Ser Asn Arg Ile Leu Thr Leu Pro Gln Arg Thr Ile Arg Gly Lys Asn
            100                 105                 110

Lys His Cys Trp Ser Thr Ser Lys Pro Thr Arg Arg Ser Arg Val Ser
        115                 120                 125

Ala Leu Asn Ile Val Arg Ser Gln Arg Gly Pro Thr Arg Met Cys Arg
130                 135                 140

Asn Ile Tyr Asp Pro Leu Leu Cys Phe Lys Leu Phe Phe Thr Asp Glu
145                 150                 155                 160

Ile Ile Ser Glu Ile Val Lys Trp Thr Asn Ala Glu Ile Ser Leu Lys
                165                 170                 175

Arg Arg Glu Ser Met Thr Ser Ala Thr Phe Arg Asp Thr Asn Glu Asp
            180                 185                 190

Glu Ile Tyr Ala Phe Phe Gly Ile Leu Val Met Thr Ala Val Arg Lys
        195                 200                 205

Asp Asn His Met Ser Thr Asp Asp Leu Phe Asp Arg Ser Leu Ser Met
210                 215                 220

Val Tyr Val Ser Val Met Ser Arg Asp Arg Phe Asp Phe Leu Ile Arg
225                 230                 235                 240

Cys Leu Arg Met Asp Asp Lys Ser Ile Arg Pro Thr Leu Arg Glu Asn
                245                 250                 255

Asp Val Phe Thr Pro Val Arg Lys Ile Trp Asp Leu Phe Ile His Gln
            260                 265                 270

Cys Ile Gln Asn Tyr Thr Pro Gly Ala His Leu Thr Ile Asp Glu Gln
        275                 280                 285

Leu Leu Gly Phe Arg Gly Arg Cys Pro Phe Arg Val Tyr Ile Pro Asn
290                 295                 300

Lys Pro Ser Lys Tyr Gly Ile Lys Ile Leu Met Met Cys Asp Ser Gly
305                 310                 315                 320

Thr Lys Tyr Met Ile Asn Gly Met Pro Tyr Leu Gly Arg Gly Thr Gln
                325                 330                 335

Thr Asn Gly Val Pro Leu Gly Glu Tyr Tyr Val Lys Glu Leu Ser Lys
            340                 345                 350

Pro Val His Gly Ser Cys Arg Asn Ile Thr Cys Asp Asn Trp Phe Thr
        355                 360                 365

Ser Ile Pro Leu Ala Lys Asn Leu Leu Gln Glu Pro Tyr Lys Leu Thr
370                 375                 380

Ile Val Gly Thr Val Arg Ser Asn Lys Arg Glu Ile Pro Glu Val Leu
385                 390                 395                 400

Lys Asn Ser Arg Ser Arg Pro Val Gly Thr Ser Met Phe Cys Phe Asp
                405                 410                 415

Gly Pro Leu Thr Leu Val Ser Tyr Lys Pro Lys Pro Ala Lys Met Val
            420                 425                 430

-continued

```
Tyr Leu Leu Ser Ser Cys Asp Glu Asp Ala Ser Ile Asn Glu Ser Thr
            435                 440                 445
Gly Lys Pro Gln Met Val Met Tyr Tyr Asn Thr Lys Gly Gly Val
450                 455                 460
Asp Thr Leu Asp Gln Met Cys Ser Val Met Thr Cys Ser Arg Lys Thr
465                 470                 475                 480
Asn Arg Trp Pro Met Ala Leu Leu Tyr Gly Met Ile Asn Ile Ala Cys
                485                 490                 495
Ile Asn Ser Phe Ile Ile Tyr Ser His Asn Val Ser Ser Lys Gly Glu
            500                 505                 510
Lys Val Gln Ser Arg Lys Lys Phe Met Arg Asn Leu Tyr Met Gly Leu
            515                 520                 525
Thr Ser Ser Phe Met Arg Lys Arg Leu Glu Ala Pro Thr Leu Lys Arg
            530                 535                 540
Tyr Leu Arg Asp Asn Ile Ser Asn Ile Leu Pro Lys Glu Val Pro Gly
545                 550                 555                 560
Thr Ser Asp Asp Ser Thr Glu Glu Pro Val Met Lys Lys Arg Thr Tyr
                565                 570                 575
Cys Thr Tyr Cys Pro Ser Lys Ile Arg Arg Lys Ala Ser Ala Ser Cys
            580                 585                 590
Lys Lys Cys Lys Lys Val Ile Cys Arg Glu His Asn Ile Asp Met Cys
            595                 600                 605
Gln Ser Cys Phe Lys Leu Lys Leu Gly Gly Ala Pro Ala Val Gly
            610                 615                 620
Gly Gly Pro Lys Ala Ala Asp Lys Pro Val Ala Thr Met Val Ser Lys
625                 630                 635                 640
Gly Glu Glu Leu Phe Thr Gly Val Val Pro Ile Leu Val Glu Leu Asp
                645                 650                 655
Gly Asp Val Asn Gly His Lys Phe Ser Val Ser Gly Glu Gly Glu Gly
            660                 665                 670
Asp Ala Thr Tyr Gly Lys Leu Thr Leu Lys Phe Ile Cys Thr Thr Gly
            675                 680                 685
Lys Leu Pro Val Pro Trp Pro Thr Leu Val Thr Thr Leu Thr Tyr Gly
            690                 695                 700
Val Gln Cys Phe Ser Arg Tyr Pro Asp His Met Lys Gln His Asp Phe
705                 710                 715                 720
Phe Lys Ser Ala Met Pro Glu Gly Tyr Val Gln Glu Arg Thr Ile Phe
                725                 730                 735
Phe Lys Asp Asp Gly Asn Tyr Lys Thr Arg Ala Glu Val Lys Phe Glu
            740                 745                 750
Gly Asp Thr Leu Val Asn Arg Ile Glu Leu Lys Gly Ile Asp Phe Lys
            755                 760                 765
Glu Asp Gly Asn Ile Leu Gly His Lys Leu Glu Tyr Asn Tyr Asn Ser
            770                 775                 780
His Asn Val Tyr Ile Met Ala Asp Lys Gln Lys Asn Gly Ile Lys Val
785                 790                 795                 800
Asn Phe Lys Ile Arg His Asn Ile Glu Asp Gly Ser Val Gln Leu Ala
                805                 810                 815
Asp His Tyr Gln Gln Asn Thr Pro Ile Gly Asp Gly Pro Val Leu Leu
            820                 825                 830
Pro Asp Asn His Tyr Leu Ser Thr Gln Ser Ala Leu Ser Lys Asp Pro
            835                 840                 845
Asn Glu Lys Arg Asp His Met Val Leu Leu Glu Phe Val Thr Ala Ala
```

```
                850               855               860
Gly Ile Thr Leu Gly Met Asp Glu Leu Tyr Lys Leu Gly Pro Glu Gln
865                 870               875               880

Lys Leu Ile Ser Glu Glu Asp Leu Asn Ser Ala Val Asp His His His
                885               890               895

His His His

<210> SEQ ID NO 5
<211> LENGTH: 36
<212> TYPE: DNA
<213> ORGANISM: Artificial Sequence
<220> FEATURE:
<223> OTHER INFORMATION: synthetic sequence-pB-11-KpnI

<400> SEQUENCE: 5
atcgggtacc ttaaccctag aaagataatc atattg                              36

<210> SEQ ID NO 6
<211> LENGTH: 75
<212> TYPE: DNA
<213> ORGANISM: Artificial Sequence
<220> FEATURE:
<223> OTHER INFORMATION: synthetic sequence-pB-5-forward

<400> SEQUENCE: 6
ggtaccccct agaaagataa tcatattgtg acgtacgtta aagataatca tgcgtaaaat    60
tgacgcatgc tcgag                                                     75

<210> SEQ ID NO 7
<211> LENGTH: 76
<212> TYPE: DNA
<213> ORGANISM: Artificial Sequence
<220> FEATURE:
<223> OTHER INFORMATION: synthetic sequence-pB-6-reverse

<400> SEQUENCE: 7
gagctcccct agaaagatag tctgcgtaaa attgacgcat gccaccgcgg tggatttaaa    60
tctcgagcat gcgtca                                                    76

<210> SEQ ID NO 8
<211> LENGTH: 34
<212> TYPE: DNA
<213> ORGANISM: Artificial Sequence
<220> FEATURE:
<223> OTHER INFORMATION: synthetic sequence-pB-12-SacI

<400> SEQUENCE: 8
cgatgagctc ttaaccctag aaagatagtc tgcg                                34
```

TRANSPOSON SYSTEM, KIT COMPRISING THE SAME, AND USES THEREOF

CROSS-REFERENCE TO RELATED APPLICATIONS

This application is the National Stage of International Application No. PCT/CN2016/109510, filed on Dec. 12, 2016, which claims the benefit of U.S. Provisional Application No. 62/267,270, filed on Dec. 14, 2015. The contents of both applications are hereby incorporated by reference in their entirety.

BACKGROUND OF THE INVENTION

1. Field of the Invention

The present disclosure in general relates to systems, kits, and methods of engineering cells to carry genes of interest; and uses of the engineered cells as therapeutic agents to treat subjects in need thereof.

2. Description of Related Art

The PiggyBac (PB) transposon is a mobile genetic element that efficiently transposes between vectors and chromosomes via a "cut and paste" mechanism. During transposition, the PB transposase recognizes transposon-specific inverted terminal repeat sequences (ITRs) located on both ends of the transposon vector and moves the contents from the original sites and efficiently integrates them into TTAA chromosomal sites. The powerful activity of the PB transposon system enables genes of interest between the two ITRs in the PB vector to be easily mobilized into target genomes.

The unique features of PB transposons include: (1) there is no cargo limit; it has been reported that the PB transposon can mobilize up to 100 kilobase-DNA fragment into the target cells; (2) the transposition process is reversible; genomes containing an inserted PB vector can be transiently transfected with a vector only expressing PB transposase so as to remove the transposons from the genome; and (3) the uses of the PB transposon are not limited to specific species; the TTAA-specific PB transposon is a highly useful transposon for genetic engineering of a wide variety of species, for example, insect cells and mammalian cells. Further, compared with the viral vectors, the PB transposon has low immunogenicity.

Immune system plays a critical role in human health. The deficiency or malfunction of immune system decreases the body's ability to eliminate abnormal body cells and invaded pathogens, causing vulnerability to tumors and infections. On the other hand, when the immune system is overly active, then the body attacks and damages its own tissues, and accordingly leading to the development of autoimmune disease and inflammation. Thus, regulating the expression, function or interaction of immune cells, e.g., introducing an exogenous gene (i) to up-regulate or down-regulate gene expression of the immune cells or (ii) to boost or suppress the function of immune cells, may provide a potential means to prevent and/or treat the immune-related diseases. However, immune cells are difficult to constantly express an exogenous gene, which limits their use in cell therapy.

Accordingly, there exists in the related art a need for an improved expression system and methods that enable an exogenous DNA sequence, e.g., a gene, to be efficiently and constantly expressed in immune cells, which may be subsequently used for cell therapy to prevent or treat immune-related diseases and/or disorders.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

Disclosed is an in vitro method for integrating an exogenous DNA sequence into the genome of a cell. The method is carried out by (i) obtaining a transposon system that includes (a) a first vector that contains a first inverted repeat having a nucleic acid sequence consisting of SEQ ID NO: 1, the exogenous DNA sequence downstream of the first inverted repeat, and a second inverted repeat downstream of the exogenous DNA sequence, the second inverted repeat having a nucleic acid sequence consisting of SEQ ID NO: 2, and (b) a second vector that contains a promoter operably linked to a nucleic acid encoding a transposase having the amino acid sequence of SEQ ID NO: 4; and (ii) introducing the first vector and the second vector into the cell. The exogenous DNA sequence is integrated into the genome of the cell by virtue of the transposase, which is expressed in the cell and catalyzes excision of the exogenous DNA sequence from the first vector and integration of the excised exogenous nucleic acid into the genome of the cell.

Also disclosed is a kit for integrating an exogenous DNA sequence into the genome of a cell. The kit contains (i) a container; (ii) a transposon system that includes (a) a first vector containing a first inverted repeat having a nucleic acid sequence consisting of SEQ ID NO: 1, a second inverted repeat having a nucleic acid sequence consisting of SEQ ID NO: 2 downstream of the first inverted repeat, and a cloning site between the first inverted repeat and the second inverted repeat for introducing the exogenous DNA sequence, and (b) a second vector that contains a promoter operably linked to a nucleic acid encoding a transposase having the amino acid sequence of SEQ ID NO: 4; and (iii) an instruction associated with the container and indicating how to use the transposon system. The transposase catalyzes excision of the exogenous DNA sequence from the first vector and integration of the excised exogenous DNA sequence into the genome of the cell.

Furthermore, a method for treating a subject having or suspected of having an immune-related disease is within the scope of the invention. The method includes integrating an exogenous DNA sequence into the genome of an immune cell using the in vitro method described above, preferably with the kit also described above, to yield an engineered immune cell, and administering an effective amount of the engineered immune cell to the subject to ameliorate or alleviate symptoms of the immune-related disease.

Many of the attendant features and advantages of the present disclosure will become better understood with reference to the following detailed description considered in connection with the accompanying drawings.

DETAILED DESCRIPTION

Figure 1:
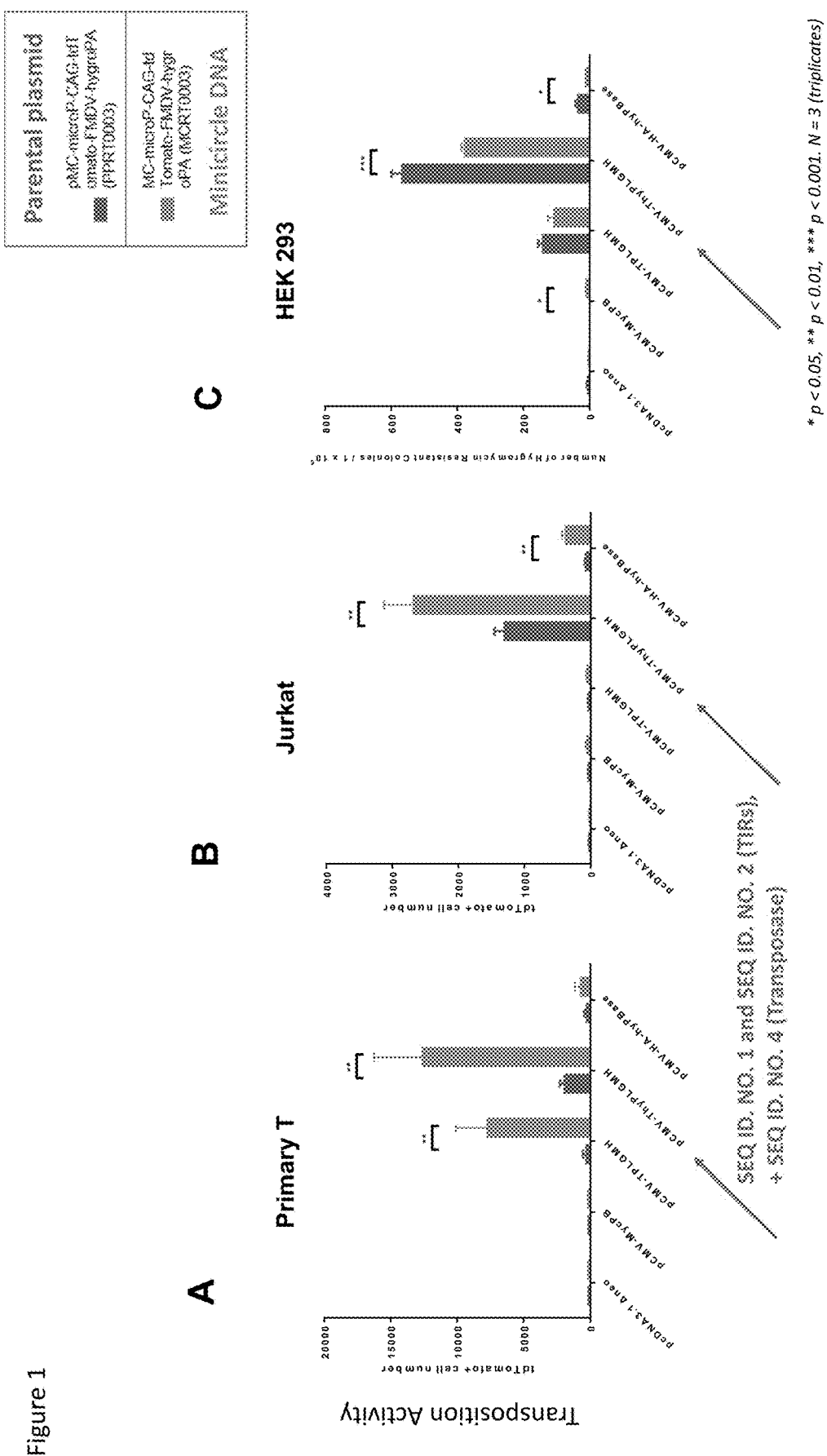
FIG. 1A is a histogram depicting the number of hygromycin-resistant colonies of HEK293 cells co-transfected with the indicated helper plasmid and DNA donor (circular form) produced by the enzyme digestion/ligation method.
FIG. 1B is a histogram depicting the number of hygromycin-resistant colonies of HEK293 cells co-transfected with the indicated helper plasmid and DNA donor (linear form) produced by the enzyme digestion/ligation method.
FIG. 1C is a histogram depicting the number of hygromycin-resistant colonies of HEK293 cells co-transfected with the indicated helper plasmid and DNA donor produced by a commercially available kit according to Example 1 below.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

1. Definitions

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used herein, the term "transposon" or "transposable element" refers to a polynucleotide that is able to change its position within a genome by excising from a donor polynucleotide, (e.g., a vector), and integrate into a target site, (e.g., a cell's genomic or extrachromosomal DNA). A transposon is a polynucleotide that includes a nucleic acid sequence flanked by cis-acting nucleotide sequences; in which at least one cis-acting nucleotide sequence is positioned 5' to the nucleic acid sequence, and at least one cis-acting nucleotide sequence is positioned 3' to the nucleic acid sequence. Cis-acting nucleotide sequences include at least one inverted repeat (IR) at each end of the transposon, to which a transposase, preferably a member of the mammalian piggyBac family of transposases, binds. In certain preferred embodiments, the transposon is a moth micro-piggyBac transposon.

As used herein, the term "transposase" refers to a polypeptide that catalyzes the excision of a transposon from a donor polynucleotide, e.g., a minicircle construct, and the subsequent integration of the transposon into the genomic or extrachromosomal DNA of a target cell. Preferably, the transposase binds an inverted repeat sequence.

As used herein, the term "polypeptide" refers to a polymer of amino acids of any length. Thus, for example, the terms peptide, oligopeptide, protein, antibody, and enzyme are included within the definition of polypeptide. The term "polypeptide" also includes post-translational modifications of the polypeptide, for example, glycosylation (e.g., the addition of a saccharide), acetylation, phosphorylation and the like.

The term "vector" as used herein refers to a nucleic acid molecule capable of transporting another nucleic acid molecule to which it has been linked. Examples of vectors include but are not limited to bacteria, plasmids, phages, cosmids, episomes, viruses, and insertable DNA fragments, i.e., fragments capable of being inserted into a host cell genome by homologous recombination.

As used herein, the term "plasmid" refers to circular, double-stranded DNA capable of accepting a foreign DNA fragment and capable of replicating in prokaryotic or eukaryotic cells.

The terms "minicircle", "minicircle DNA" and "minicircle nucleic acid sequence" are interchangeable, and are used to refer to a nucleic acid sequence typically devoid of any of plasmid/vector backbone sequences required for replication, such as the prokaryotic antibiotic resistance gene and the prokaryotic origin of replication. Minicircles can be generated in vivo from bacterial plasmids by site-specific intramolecular recombination between recombinase recognition sites in the plasmid, yielding a minicircle DNA vector devoid of bacterial plasmid backbone DNA. According to one embodiment of the present disclosure, the present minicircle is prepared by the enzyme digestion/ligation method. According to another embodiment of the present disclosure, the present minicircle is prepared by a commercially available kit, that is, Minicircle DNA Production kit (System Biosciences, CA, USA).

As used herein, the term "introduce" refers to the introduction of a polynucleotide (e.g., the minicircle nucleic acid sequence or the helper vector of the present transposon system) into a cell or organism. The nucleic acid of the polynucleotide may be in the form of naked DNA or RNA, associated with various proteins, or incorporated into a vector. The term "introduce" as used herein is intended to convey the broadest possible meaning and encompass the introduction, for example by transfection method (introducing a polynucleotide into eukaryotic cells by physical and/or chemical treatment), transformation method (introducing a polynucleotide into prokaryotic cells by physical and/or chemical treatment), viral method/viral transduction method (introducing a polynucleotide into eukaryotic and/or prokaryotic cells by a virus or a viral vector), conjugation method (introducing a polynucleotide from one cell to another cell by direct cell-to-cell contact or by a cytoplasmic bridge between the cells), and fusion method (fusing two cells, including homotypic cell fusion and heterotypic cell fusion).

The term "engineer" as used herein refers to any manipulation of a cell that results in a detectable change in the cell, wherein the manipulation includes, but is not limited to, inserting a polynucleotide and/or polypeptide heterologous/homologous to the cell and mutating a polynucleotide and/or polypeptide native to the cell.

The term "transposition" as used herein refers to a complex genetic rearrangement process involving the movement or copying of a polynucleotide (transposon) from one location and insertion into another, often occurred within a genome, or between genomes, DNA constructs (such as plasmids, bacmids, and cosmids) or genome and DNA construct. According to the embodiments of the present disclosure, the transposition is occurred between the genome and the DNA construct, in which the polynucleotide (e.g., the expression cassette of the present transposon system) is transferred from the minicircle nucleic acid sequence of the present transposon system to the genome of host cells (e.g., the immune cells).

The term "transposition efficacy" as used herein refers to the number of host cells, which contain the introduced polynucleotide, within a population of host cells. In general, the transposition efficacy can be determined by transfecting a polynucleotide encoding a reporter gene, for example, β-gal, into a population of target cells. Thus, the transfection efficiency can be determined by assaying for the gene product encoded by the introduced polynucleotide; for example, by measuring the number of cell having β-gal activity. According to one embodiment of the present disclosure, the introduced polypeptide is a hygromycin-resistance gene, and accordingly the transposition efficacy can be determined by measuring the number of cells resistant to hygromycin.

As used herein, the term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

The term "immune-related disease" as used herein refers to a disease and/or condition in which the immune system is involved in the pathogenesis of the disease, or in which appropriate stimulation or inhibition of the immune system can result in treatment and/or protection from the disease. Exemplary immune-related disease treatable by the present invention includes, but is not limited to, tumor, infectious disease, allergy, autoimmune disease, graft-versus-host disease, or inflammatory disease.

The term "subject" refers to a mammal including the human species that is treatable with methods of the present invention. The term "subject" is intended to refer to both the male and female gender unless one gender is specifically indicated.

2. Description of the Invention

In general, the present disclosure relates to systems, methods and/or kits for engineering cells to carry genes of interest (e.g., genes of therapeutic proteins). The engineered cells are then used as a therapeutic agent to treat a patient, whom is suffering from a disease and/or disorder treatable by the products of the genes of interest.

As mentioned above, an in vitro method for integrating an exogenous DNA sequence into the genome of a cell is provided. The exogenous DNA sequence can encode an antibiotic resistance protein, an siRNA, a reporter protein, a cytokine, a kinase, an antigen, an antigen-specific receptor, a cytokine receptor, or a suicide polypeptide. For example, the exogenous DNA sequence can encode a receptor specific to a tumor-associated antigen. A T-cell engineered via the method is capable of recognizing and specifically killing the tumor cells expressing the tumor-associated antigen. In another example, the exogenous DNA sequence encodes a hygromycin-resistance protein so that a hygromycin-resistance cell line can be established. Alternatively, the exogenous DNA sequence may not possess any biological function, and can be used to interrupt the function of another gene by inserting itself into an essential gene, thereby interrupting its function. For example, the exogenous DNA sequence can encode an anti-sense RNA for PD-1 or T cell specific receptor (TCR) gene silencing.

The method described above is carried out by first obtaining a transposon system.

The transposon system includes a first vector that contains a first inverted repeat having a nucleic acid sequence consisting of SEQ ID NO: 1, an exogenous DNA sequence downstream of the first inverted repeat, and a second inverted repeat downstream of the exogenous DNA sequence, the second inverted repeat having a nucleic acid sequence consisting of SEQ ID NO: 2. The first vector can further include a non-prokaryotic promoter operably linked to the exogenous DNA sequence. The non-prokaryotic promoter can be, e.g., the cytomegalovirus promoter, the Rous sarcoma virus promoter, the simian virus 40 promoter, the mouse mammary tumor virus promoter, the phosphoglycerate kinase promoter, the chicken beta-actin promoter, the elongation factor 1-alpha promoter, the human H1 promoter, and the U6 promoter. As an example, the first vector further includes an enhancer, a silencer, or an insulator.

In a particular embodiment, the first vector is a minicircle DNA lacking prokaryotic sequences required for bacterial replication. The minicircle DNA can have a length of 500-1,500 bp exclusive of the exogenous DNA sequence. For example, the minicircle DNA can have a length of 700-1,200 bp or 800-1,000 bp exclusive of the exogenous DNA sequence.

In general, prokaryotic DNA is regarded as an immune-stimulating antigen, which would elicit an immune response in a host leading to a decrease in the expression efficacy of the exogenous DNA carried by the first vector. Accordingly, the lack of prokaryotic sequences in the minicircle DNA renders the present transposon system more efficient in terms of introducing and expressing the exogenous DNA in a host cell, e.g., a eukaryotic cell, as compared with that of other transposon/expression systems that include prokaryotic DNA sequences. Furthermore, the transposon system described above is smaller in size as compared with that of typical transposon/expression systems, due to the absence of prokaryotic DNA sequences in the minicircle DNA.

The transposon system also includes a second vector, i.e., a helper plasmid that contains a promoter operably linked to a nucleic acid encoding a transposase. The transposase recognizes and binds to the first inverted repeat and the second inverted repeat in the first vector. The transposase can be, e.g., ThyPLGMH, mycPBase, TPLGMH, or HAhyPBase. In a particular embodiment, the transposase has the amino acid sequence of SEQ ID NO: 4 that is encoded by SEQ ID NO: 3. The helper vector may be prepared in accordance with methods known in the art, such as that described by Yaa-Jyuhn James Meir et. al. (A versatile, highly efficient, and potentially safer piggyBac transposon system for mammalian genome manipulations, FASEB, 2013: 27, 4429-4443).

The promoter in the second vector is selected from the cytomegalovirus promoter, the Rous sarcoma virus promoter, the simian virus 40 promoter, the mouse mammary tumor virus promoter, the phosphoglycerate kinase promoter, the chicken beta-actin promoter, the elongation factor 1-alpha promoter, the human H1 promoter, and the U6 promoter. In a particular embodiment, the promoter is the cytomegalovirus promoter.

To carry out the method, the first vector and the second vector are introduced into a cell. This can be accomplished using techniques including, but not limited to, calcium phosphate co-precipitation, electroporation, nucleofection, cell squeezing (gently squeezing the cell membrane), sonoporation (inducing pore formation in cell membrane by high-intensity ultrasound), optical transfection (generating a tiny hole in cell membrane by highly focused laser), impalefection (inserting into a cell DNA bound to the surface of a nanofiber), gene gun ("shooting" into the cell nucleus DNA coupled to a nanoparticle of an inert solid), magnetofection (using magnetic force to deliver DNA into target cells), viral transduction (using viruses as a carrier to deliver DNA into target cells), or transfection via a dendrimer, a liposome, or a cationic polymer. In one example, the transposon system is introduced into a cell via a non-liposomal chemical method, namely, FuGENE® HD transfection. In another example, the transposon system is introduced into a cell via nucleofection. In a particular embodiment of the method, the first vector of the transposon system is linearized, for instance, using a restriction enzyme, prior to introducing it into a cell.

The first vector and the second vector are introduced into the cell in a ratio ranging from 2:1 to 1:1 by weight. According to one embodiment, the exogenous DNA is introduced into an epithelial cell and the ratio between the first vector, e.g., minicircle DNA and the second vector is 2:1 to 1:1 by weight. According to another embodiment, the exogenous DNA is introduced into an immortal T cell and the ratio between the minicircle nucleic acid sequence and the helper vector is about 2:1 to 1:1 by weight. In still another embodiment, the exogenous DNA is introduced into a primary T cell and the ratio between the minicircle nucleic acid sequence and the helper vector is about 2:1 to 1:1 by weight.

The exogenous DNA sequence is integrated into the genome of the cell by virtue of the transposase, which is expressed in the cell by the second vector and catalyzes excision of the exogenous DNA sequence from the first vector and integration of the excised exogenous DNA into the genome of the cell.

The cell used in the above method can be an immune cell. More specifically, the immune cell can be a T cell, a B cell, a dendritic cell, a macrophage, or a mast cell.

In another aspect, the cell is a stem cell. The stem cell can be derived from, e.g., bone marrow, adipose tissue, peripheral blood, umbilical cord blood, or dental pulp. In a particular method, the cell is a human cell.

To carry out the above method, a kit for integrating an exogenous DNA sequence into the genome of a cell is provided. The kit contains a container, which comprises the present transposon system described above; and an instruction associated with the container and indicating how to use the present transposon system. As mentioned above, the present transposon system includes a first and a second vectors.

The first vector includes a first inverted repeat having a nucleic acid sequence consisting of SEQ ID NO: 1, a second inverted repeat having a nucleic acid sequence consisting of SEQ ID NO: 2 downstream of the first inverted repeat, and a cloning site between the first inverted repeat and the second inverted repeat for introducing an exogenous DNA sequence.

The first vector in the kit can further include a non-prokaryotic promoter downstream of the first inverted repeat and upstream of the cloning site. The exogenous DNA can be inserted into the cloning site such that the non-prokaryotic promoter is operably linked to the exogenous DNA sequence. The non-prokaryotic promoter can be, e.g., the cytomegalovirus promoter, the Rous sarcoma virus promoter, the simian virus 40 promoter, the mouse mammary tumor virus promoter, the phosphoglycerate kinase promoter, the chicken beta-actin promoter, the elongation factor 1-alpha promoter, the human H1 promoter, and the U6 promoter. In one example, the first vector further includes an enhancer, a silencer, or an insulator.

The kit also includes a second vector, i.e., a helper plasmid, which contains a promoter operably linked to a nucleic acid encoding a transposase. The transposase can be, e.g., ThyPLGMH, mycPBase, TPLGMH, or HAhyPBase In a particular embodiment, the transposase has the amino acid sequence of SEQ ID NO: 4.

The second vector in the kit, like the second vector used in the in vitro method set forth, supra, contains a promoter selected from the cytomegalovirus promoter, the Rous sarcoma virus promoter, the simian virus 40 promoter, the mouse mammary tumor virus promoter, the phosphoglycerate kinase promoter, the chicken beta-actin promoter, the elongation factor 1-alpha promoter, the human H1 promoter, and the U6 promoter. In a particular embodiment, the promoter is the cytomegalovirus promoter.

As used herein, "instruction" includes a pamphlet, a recording, a diagram, or any other medium of expression (e.g., tape, CD, VCD or DVD) that can be used to communicate or teach the user how to use the present transposon system. The instruction can be affixed to the container, or is packed independently from the container that comprises the present transposon system.

The kit described herein may further include a buffer solution for stabilizing the transposon system and/or for performing cell transfection. Buffer solutions can be, e.g., phosphate-buffered saline, Tris-based saline, Tris-EDTA buffer, 4-(2-hydroxyethyl)-1-piperazineethanesulfonic acid buffer, or (N,N-bis(2-hydroxyethyl)-2-amino ethanesulfonic acid (BES) buffer.

As mentioned above, a method for treating a subject having or suspected of having an immune-related disease is provided. The method includes engineering cells with the aid of the kit described above to carry a gene suitable for the treatment of the immune-related disease and administering an effective amount of the engineered cells for the treatment of the immune-related disease. In an example, the gene is a chimeric antigen receptor (CAR) against CD19 for engineering CAR T cells for treating acute lymphoblastic leukemia.

The subject having or suspected of having an immune-related disease is a mammalian animal, including human, mouse, rat, rabbit, monkey, and pig. In a specific aspect, the subject is a human. In the case when the subject being treated is a human, the introduced/transferred immune cell of the present method is preferably derived from the subject himself/herself. Alternatively, the introduced/transferred immune cell of the present method is derived from a donor.

According to some embodiments of the present disclosure, the present method is useful in treating an immunosuppression disease, such as tumor or infectious disease. In these embodiments, the present transposon system may comprise an immune-enhancing gene so as to enhance the immune response in the subject.

According to other embodiments of the present disclosure, the present method is useful in treating a disease caused by a hyperactive immune response (e.g., autoimmune disease) or an inappropriate immune response (e.g., allergy, graft-versus-host disease, or inflammatory disease). In the embodiments, the present transposon system comprising an immune-suppressive gene is capable of inhibiting the immune response in the subject.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLES

Materials and Methods
Cell Culture

Human embryonic kidney cell line 293 (HEK 293), human JK immortal T-lymphocytes (Jurkat T), and primary human T cells were used in the present study. The HEK293 cells were cultured in MEM medium containing 10% FBS, 2 mM L-glutamine, 1× nonessential amino acids, 1× penicillin/streptomycin, and 1 mM sodium pyruvate. The Jurkat T cells and the primary human T cells were cultured in RPMI1640 medium containing 2 mM L-glutamine, 10% FBS, 1 mM sodium pyruvate, and 0.1 mM nonessential amino acids. All cells were maintained at 37° C. with 5% $CO_2$.

Production of Conditioned Medium

Jurkat cells were cultured in a fresh medium at the density of $2\times10^6$/mL for 24 hrs., then the culture medium was collected, filtered and used as the conditioned medium.

Generation of Plasmids and/or Expression Constructs
pBS-Cassette

The DNA fragment containing the hygromycin resistance gene driven by the SV40 promoter was excised from pcDNA3.1_hygro_LacZ vector (Invitrogen). After XmnI and SapI digestion, the DNA fragment was cloned into the SmaI site of pBlueScript SKII to complete the construction of pBS-hygro. To further insert the kanamycin resistance gene and the ColE1 origin of replication, the ApoI_AflIII fragment of pZErO-2.1 (Invitrogen) was cloned into the EcoRV site of pBS-hygro to complete the construction of the pBS-cassette.

Mini-piggyBac_Long

The pBS-cassette was digested with restriction enzyme SmaI and EcoRV, followed by inserting the digested fragment into pXLBacIIPUbnIsEGFP, which was derived from pBSII-ITR1. The construct thus produced, mini-piggyBac_long, had terminal repeats (TR) of 308 bp and 238 bp at its 5'- and 3'-ends, respectively.

The linear form of mini-piggyBac_long is prepared by digesting the mini-piggyBac_long with XmnI.

Mini-piggyBac_Short

The mini-piggyBac_long construct was digested with PciI and AclI, filled-in by klenow (NE Biolabs) and self-ligated by T4 DNA ligase (NE Biolabs), so as to produce mini-piggyBac_short, which did not contain the ampicillin resistance gene and the f1 replication origin.

The linear form of mini-piggyBac_short is prepared by digesting the mini-piggyBac_short with Bgl I.

Micro-piggyBac_Long

The short piggyBac terminal repeat domains (TRD) (i.e. 746~808 3' LTR and 1426~1460 5' LTR as in pXL-BacII) were obtained from the PCR mixture consisting of the following four pairs of primers; pB-11-KpnI (SEQ ID NO: 5), pB-S-forward (SEQ ID NO: 6), pB-6-reverse (SEQ ID NO: 7), and pB-12-SacI (SEQ ID NO: 8). The resulting amplicon containing both 67 bp 5' and 40 bp 3' TRD with SwaI and Xho I restriction sites in between was cloned into pBS-SKII through Kpn I and Sac I restriction sites to obtain pPBendAATT. The expression cassette obtained from the pBS-cassette described above was inserted between short piggyback TRDs in pPBendAATT through the blunt-ended Xho I site to produce micro-piggyBac_long.

The linear form of micro-piggyBac_long is prepared by digesting the micro-piggyBac_long with XmnI.

Micro-piggyBac_Short

The micro-piggyBac_long was digested with Acc65I and AflIII to remove the ampicillin resistance gene and the f1 replication origin. The remaining DNA fragment was blunt-ended followed by self-ligation to generate the construct of micro-piggyBac_short, which did not contain the ampicillin resistance gene and the f1 replication origin. This construct is also designated as the minicircle cassette.

The linear form of micro-piggyBac_short is prepared by digesting micro-piggyBac_short with XmnI Minicircle-microPB-Cassette Alternatively, the micro-piggyBac_short, i.e., minicircle cassette, can be prepared using the MC-Easy circle Minicircle DNA Production kit. In this method, the micro-piggyBac_long was digested with KpnI, SacI, and XmnI, the KpnI-SacI fragment (3993 bp) containing the left (microL) and right (microR) inverted repeats of micro-piggyBac was blunt-ended and inserted into the EcoRV site of pMC.BE-SPX-MCS1 so as to produce pMC-microPB-cassette. The minicircle-microPB-cassette was prepared from the pMC-microPB-cassette using the MC-Easy circle Minicircle DNA Production kit by following the manufacturer's protocol. The minicircle-microPB-cassette thus produced did not contain the ampicillin resistance gene and the f1 replication origin.

Helper Plasmid

The helper plasmids pCMV-ThyPLGMH, pCMV-mycPBase, pCMV-TPLGMH, and pCMV-HAhyPBase were constructed in accordance with the protocol described by Yaa-Jyuhn James Meir et. al. (A versatile, highly efficient, and potentially safer piggyBac transposon system for mammalian genome manipulations, FASEB, 2013: 27, 4429-4443). The content of this publication is hereby incorporated by reference in its entirety.

Transposition Assay

HEK293 Cells

Cells at 80% confluence were harvested and seeded into individual wells of 24-well plates at a density of $1\times10^5$ cells/well 18 hours before transfection. For each transfection, a total of 300 ng DNA mixture were transfected using Fugene 6 (Roche, Florence, S.C.). Each DNA mixture contained 100 ng of helper plasmid (i.e., pCMV-Thy-PLGMH, pCMV-mycPBase, pCMV-TPLGMH, or pCMV-HAhyPBase), various amounts of DNA donor (i.e., mini-piggyBac_long, mini-piggyBac_short, micro-piggyBac_long, micro-piggyBac_short, pMC-microPB-cassette, or minicircle-microPB-cassette; the amount of the smallest donor was set to be 100 ng) and pcDNA3.1 for a total of 300 ng of DNA. For each transfection reaction, one fifth of the transfected cells were transferred to 100-mm plates followed by hygromycin selection for 14 days. To count the clones, cells were fixed with PBS containing 4% paraformaldehyde for 10 min and then stained with 0.2% methylene blue for 1 hour. After 14 days of hygromycin selection, only colonies 0.5 mm in diameter were counted.

Jurkat T Cells

Cells were seeded at $1\times10^6$/mL 24 hours before nucleofection. For each nucleofection reaction, a total of 6 µg of DNA was used to transfect $1\times10^6$ cells. Each DNA mixture contained 2.5 µg of helper plasmid (i.e., pCMV-Thy-PLGMH, pCMV-mycPBase, pCMV-TPLGMH, or pCMV-HAhyPBase), various amounts of DNA donor (i.e., mini-piggyBac_long, mini-piggyBac_short, micro-piggyBac_long, micro-piggyBac_short, pMC-microPB-cassette, or minicircle-microPB-cassette; the amount of the smallest donor was set to be 2.0 µg) and pcDNA3.1 for a total of 6 µg DNA. 24 hours after nucleofection, 30 live cells in 50 µL of conditioned medium described above with 1.2 mg hygromycin were seeded into each well of a 96-well plate. Every two to three days, an equal volume of conditioned medium was added gently into each well without disturbing the cell clusters. For each reaction, a total of 10,200 live cells were subjected to hygromycin selection. Transposition activity was determined by counting the total number of cell clusters for each reaction under a light microscope 6 or 7 days after hygromycin selection.

Primary T Cells

One day before nucleofection, human primary cells (CD8$^+$CD45RA$^+$) were thawed in RPMI complete medium. After overnight culture, cells were harvested and subjected to nucleofection. For each nucleofection reaction, a total of 2.2 µg of DNA were used to transfect $1\times10^5$ cells in 20 µl of ALL-IN-ONE nucleofection buffer (GF1001, GenomeFrontier, Biosciences). Each DNA mixture contained 0.8 µg of helper plasmid (i.e. pCMV-HAhyPBase or pCMV-Thy-PLGMH), various amounts of donor plasmid (i.e., mini-piggyBac_long, mini-piggyBac_short, micro-piggyBac_long, or micro-piggyBac_short; the amount of the largest donor was set to be 1.4 µg) and pcDNA3.1 for a total amount of 2.2 µg of DNA. 24 hours after nucleofection, total cells transfected in each reaction were cultured in 500 ul of RPMI 1640 complete medium with the addition of stimuli (IL-2 (50 ug/ml) and PHA) and hygromycin (1.0 mg/ml). Transposition activity was determined by counting the total number of surviving cells 22 days after hygromycin selection.

Example 1: Transposition Activity in HEK293 Cells

The transposition activities of DNA donors and helper plasmid were analyzed in this example. The results are depicted in FIGS. 1A-1C.

As shown in FIG. 1A, no matter what DNA donor was co-transfected, the cells transfected with pCMV-Thy-PLGMH resulted in more hygromycin-resistant cells, as compared with those transfected with pcDNA3.1, pCMV-TPLGMH, or pCMV-mycPBase. The data indicated that ThyPLGMH exhibited the strongest transposition activity among the transposases tested. As to the DNA donor, all four tested DNA donors (i.e., mini-piggyBac_long, mini-piggyBac_short, micro-piggyBac_long, and micro-piggyBac_short) exhibited similar transposition activity in HEK293 cells (FIG. 1A). Surprisingly, when the DNA donors were transfected into HEK293 cells in their linearized forms, the transposition activity of micro-piggyBac (i.e., micro-piggyBac_short or micro-piggyBac_long) was obviously higher than that of mini-piggyBac (i.e., mini-piggyBac_short or mini-piggyBac_long) (FIG. 1B), in which micro-piggyBac_short exhibited the strongest transposition activity.

The transposition activity was further examined using the minicircle prepared with the MC-Easy circle Minicircle DNA Production kit. The data shown in FIG. 1C indicated that the activity of minicircle-microPB-cassette was about 2.7-fold higher than that of pMC-microPB-cassette when they were co-transfected with pCMV-ThyPLGMH.

Taken together, these data indicated that the transposition activity decreased as the total length or the TRD of DNA donor increased; and ThyPLGMH possessed higher transposition activity than other transposases tested. Accordingly, compared with other DNA donors and helper plasmids, the combination of pCMV-ThyPLGMH and micro-piggyBac minicircle (i.e., either micro-piggyBac_short or minicircle-microPB-cassette) produced the highest transposition efficacy in HEK293 cells.

Example 2: Transposition Activity in Jurkat T Cells

The transposition activity of pCMV-ThyPLGMH and micro-piggyBac minicircle was further examined in Jurkat T cells. The results are depicted in FIGS. 2A-2B.

Figure 2A:
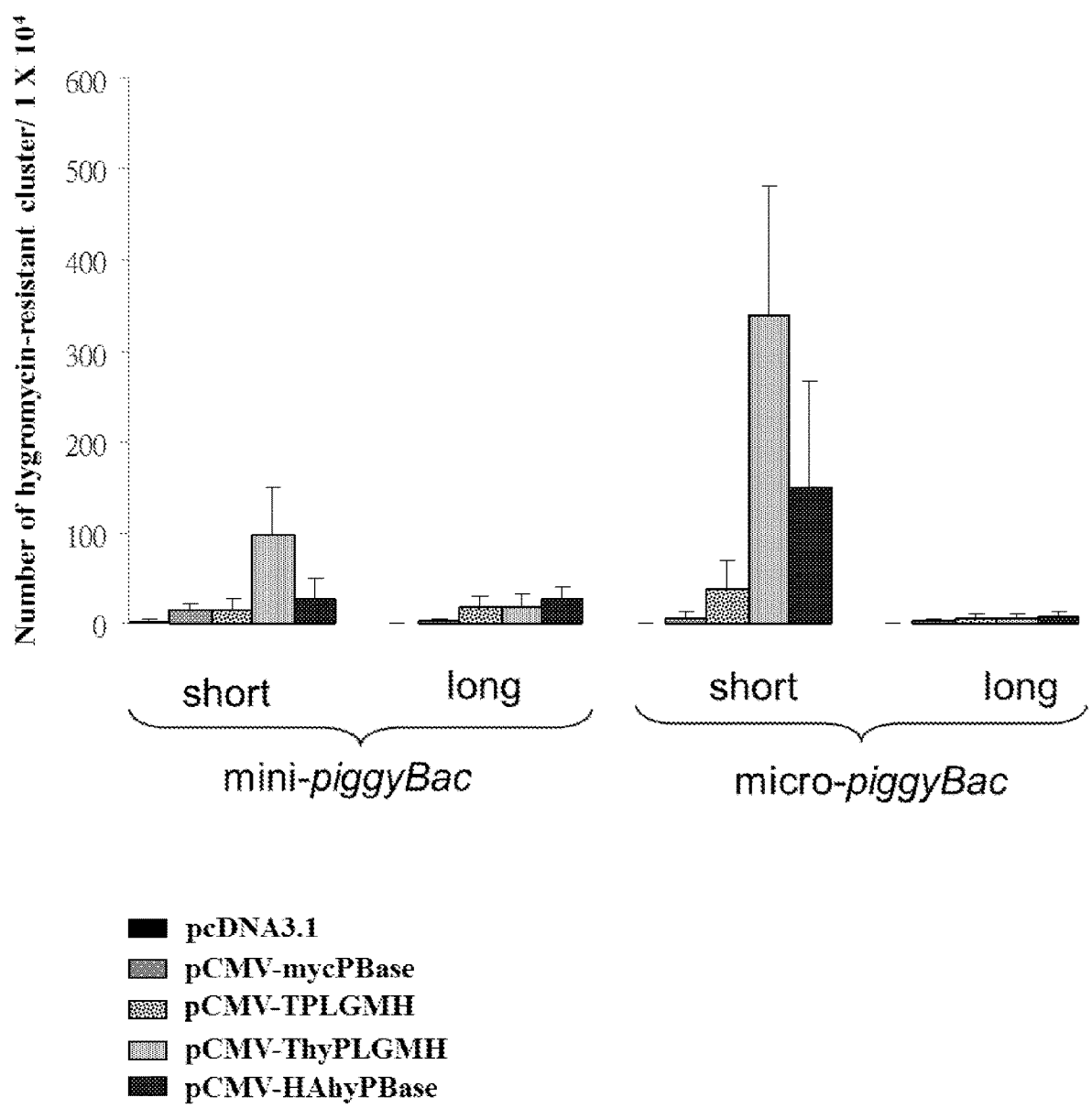
FIG. 2A is a histogram depicting the number of hygromycin-resistant colonies of Jurkat T cells co-transfected with the indicated helper plasmid and DNA donor produced by the enzyme digestion/ligation method.

As shown in FIG. 2A, the number of hygromycin-resistant colonies obtained from cells co-transfected with pCMV-ThyPLGMH and micro-piggyBac_short was significantly higher than that of cells co-transfected with other DNA donors and helper plasmids.

Figure 2B:
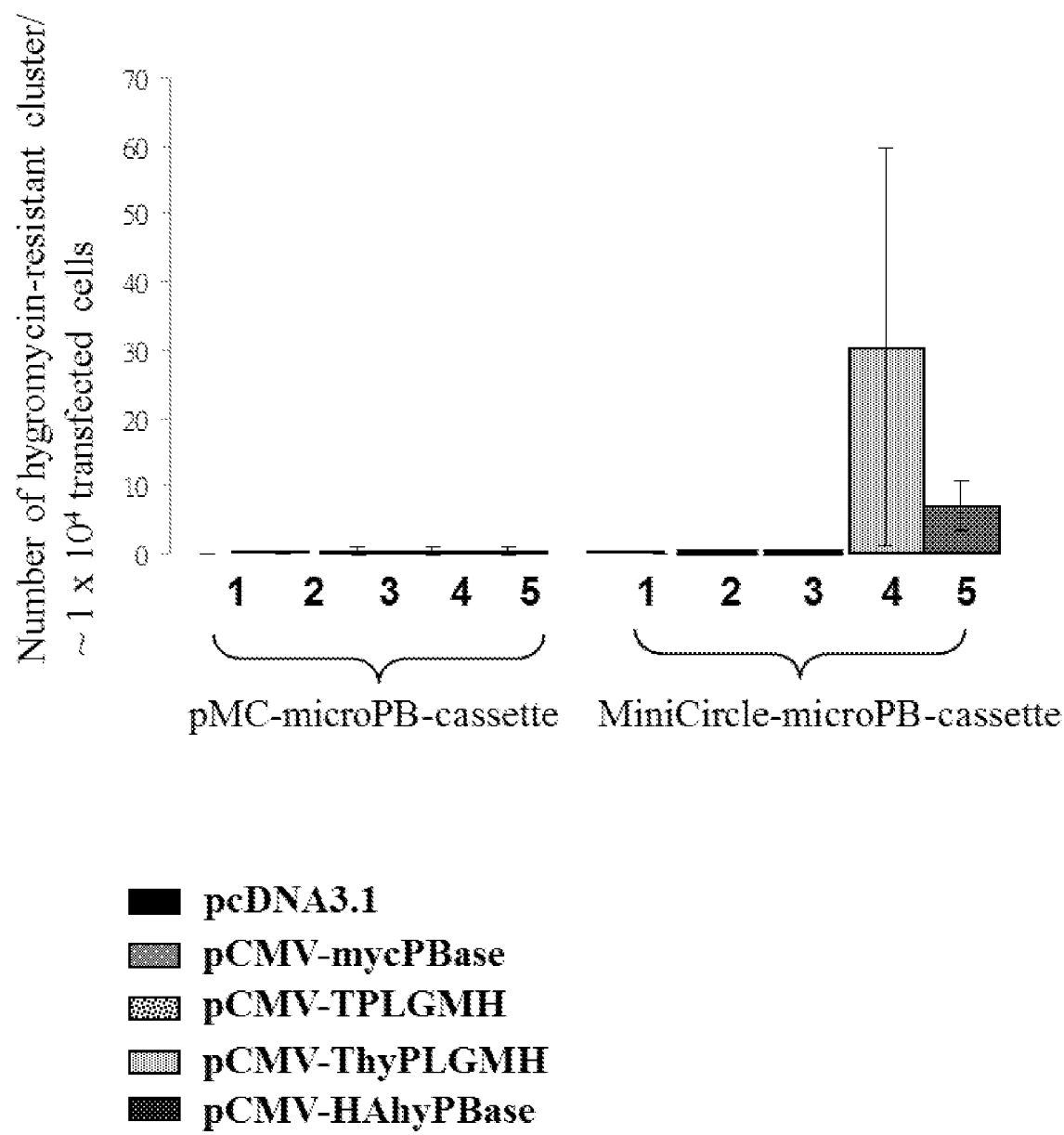
FIG. 2B is a histogram depicting the number of hygromycin-resistant colonies of Jurkat T cells co-transfected with the indicated helper plasmid and DNA donor produced by a commercially available kit according to Example 2 below.

Similar to the finding shown in FIG. 1C, the combination of pCMV-ThyPLGMH and minicircle-microPB-cassette produced the highest transposition efficacy, compared with other DNA donor/helper plasmid combinations (FIG. 2B).

Example 3: Transposition Activity in Primary Human T Cells

In addition to the cell lines described above, i.e., HEK293 cells and Jurkat T cells, the transposition activity of specific DNA donors and helper plasmids were further analyzed in primary human T cells.

Figure 3:
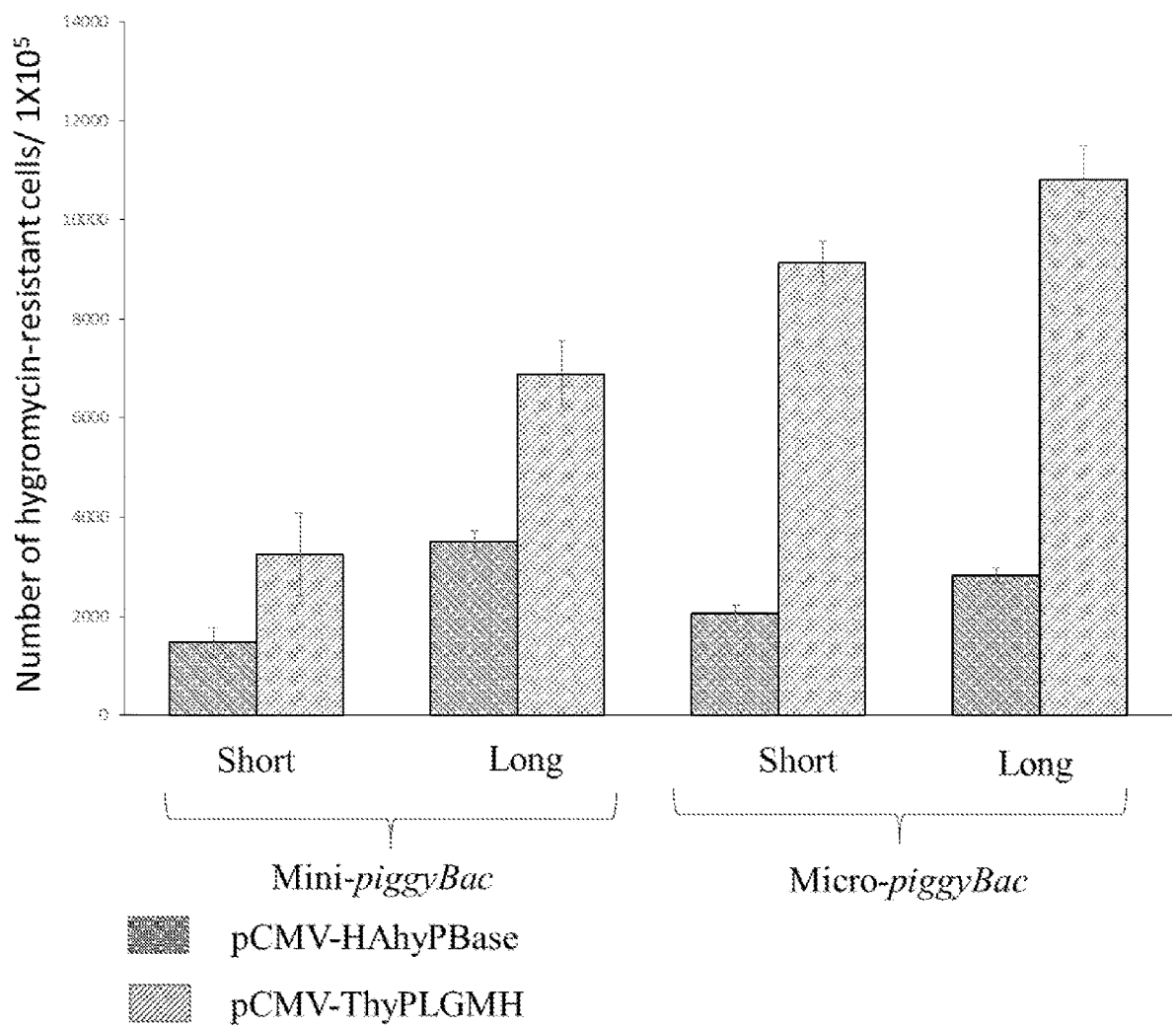
FIG. 3 is a histogram depicting the transposition efficacy of the indicated DNA donor and helper plasmid co-transfected into primary human T cells according to Example 3 below.

As depicted in FIG. 3, the best transposition activity in human primary T cells was observed in cells transfected with pCMV-ThyPLGMH with either the short or long form of micro-piggyBac, i.e., micro-piggyBac_short or micro-piggyBac_long.

In conclusion, the present disclosure provides a transposon system and method for integrating an exogenous gene into the genome of a cell, especially in an immune cell. Compared with the combinations of other DNA donors and helper plasmids, the combination of pCMV-ThyPLGMH and micro-piggyBac minicircle (either produced by enzyme digestion/ligation method (i.e., micro-piggyBac_short) or produced by MC-Easy circle Minicircle DNA Production kit (i.e., minicircle-microPB-cassette)) or micro-piggyBac_long would produce the highest transposition efficacy. Accordingly, the present disclosure provides a potential means to treat different disease (e.g., an immune-related disease) via efficiently transporting a therapeutic gene into the subject in need thereof.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. An in vitro method for integrating an exogenous DNA sequence into the genome of a cell, the method comprising:

(i) obtaining a transposon system that includes a first vector containing:

a first inverted repeat having a nucleic acid sequence consisting of SEQ ID NO: 1, the exogenous DNA sequence downstream of the first inverted repeat, and a second inverted repeat downstream of the exogenous DNA sequence, the second inverted repeat having a nucleic acid sequence consisting of SEQ ID NO: 2, and a second vector that contains a promoter operably linked to a nucleic acid encoding a transposase having the amino acid sequence of SEQ ID NO: 4; and (ii) introducing the first vector and the second vector into the cell, whereby the exogenous DNA sequence is integrated into the genome of the cell, wherein the cell is a T cell, the first vector is a minicircle DNA lacking prokaryotic sequences required for bacterial replication, and the transposase is expressed in the T cell and catalyzes excision of the exogenous DNA sequence from the first vector and integration of the excised exogenous nucleic acid into the genome of the T cell with higher transposition efficacy than that obtained from a corresponding first vector containing prokaryotic sequences required for bacterial replication.

2. The method of claim 1, wherein the exogenous DNA sequence encodes an antibiotic resistance protein, an siRNA, a reporter protein, a cytokine, a kinase, an antigen, an antigen-specific receptor, a cytokine receptor, or a suicide polypeptide.

3. The method of claim 2, wherein the first vector further comprises a non-prokaryotic promoter operably linked to the exogenous DNA sequence.

4. The method of claim 3, wherein the non-prokaryotic promoter is selected from the group consisting of cytomegalovirus promoter, Rous sarcoma virus promoter, simian virus 40 promoter, mouse mammary tumor virus promoter, phosphoglycerate kinase promoter, chicken beta-actin promoter, elongation factor I-alpha promoter, human H1 promoter, and U6 promoter.

5. The method of claim 2, wherein the first vector further comprises an enhancer, a silencer, or an insulator.

6. The method of claim 1, wherein the promoter in the second vector is selected from the group consisting of cytomegalovirus promoter, Rous sarcoma virus promoter, simian virus 40 promoter, mouse mammary tumor virus promoter, phosphoglycerate kinase promoter, chicken beta-actin promoter, elongation factor 1-alpha promoter, human H1 promoter, and U6 promoter.

7. The method of claim 1, further comprising linearizing the first vector prior to the introducing step.

8. The method of claim 1, wherein the first vector and the second vector are introduced into the T cell by calcium phosphate co-precipitation, electroporation, nucleofection, cell squeezing, sonoporation, optical transfection, impalefection, gene gun, magnetofection, viral transduction, or transfection via a dendrimer, a liposome, or a cationic polymer.

9. The method of claim 1, wherein the T cell is a human T cell.

10. A kit for integrating an exogenous DNA sequence into the genome of a cell, the kit comprising:
a container;
a transposon system that includes
    a first vector containing:
        a first inverted repeat having a nucleic acid sequence consisting of SEQ ID NO: 1,
        a second inverted repeat having a nucleic acid sequence consisting of SEQ ID NO: 2 downstream of the first inverted repeat, and
        a cloning site between the first inverted repeat and the second inverted repeat for introducing the exogenous DNA sequence, and
    a second vector that contains a promoter operably linked to a nucleic acid encoding a transposase having the amino acid sequence of SEQ ID NO: 4; and
an instruction associated with the container and indicating how to use the transposon system;
wherein the cell is a T cell, the first vector is a minicircle DNA lacking prokaryotic sequences required for bacterial replication, and the transposase catalyzes excision of the exogenous DNA sequence from the first vector and integration of the excised exogenous DNA sequence into the genome of the T cell with higher transposition efficacy than that obtained from a corresponding first vector containing prokaryotic sequences required for bacterial replication.

11. The kit of claim 10, wherein the promoter in the second vector is selected from the group consisting of cytomegalovirus promoter, Rous sarcoma virus promoter, simian virus 40 promoter, mouse mammary tumor virus promoter, phosphoglycerate kinase promoter, chicken beta-actin promoter, elongation factor 1-alpha promoter, human H1 promoter, and U6 promoter.

12. The kit of claim 10, wherein the first vector further comprises a non-prokaryotic promoter downstream of the first inverted repeat and upstream of the cloning site, wherein the non-prokaryotic promoter is selected from the group consisting of cytomegalovirus promoter, Rous sarcoma virus promoter, simian virus 40 promoter, mouse mammary tumor virus promoter, phosphoglycerate kinase promoter, chicken beta-actin promoter, elongation factor 1-alpha promoter, human H1 promoter, and U6 promoter.

* * * * *